United States Patent [19]

Antons et al.

[11] Patent Number: 5,475,142

[45] Date of Patent: Dec. 12, 1995

[54] PROCESS FOR PREPARING ALKYL-(3-CHLOROPHENYL)-SULPHONES

[75] Inventors: Stefan Antons; Helmut Fiege; Werner Bussmann, all of Leverkusen; Hartmut Richter, Langenfeld, all of Germany

[73] Assignee: Bayer Aktiengesellschaft, Leverkusen, Germany

[21] Appl. No.: 288,632

[22] Filed: Aug. 10, 1994

[30] Foreign Application Priority Data

Aug. 17, 1993 [DE] Germany ............... 43 27 571.0

[51] Int. Cl.$^6$ ............... C07C 317/14
[52] U.S. Cl. ............... 568/28
[58] Field of Search ............... 568/28

[56] References Cited

U.S. PATENT DOCUMENTS

| | | | |
|---|---|---|---|
| 4,675,447 | 6/1987 | Ludvik | 568/28 |
| 5,189,224 | 2/1993 | Baba et al. | 568/28 |
| 5,241,120 | 8/1993 | Sell et al. | 568/28 |

FOREIGN PATENT DOCUMENTS

| | | | |
|---|---|---|---|
| 949054 | 9/1956 | Germany | 568/28 |
| 260493 | 9/1988 | Germany. | |
| 9107384 | 11/1990 | WIPO | 568/28 |
| WO9214700 | 9/1992 | WIPO. | |

OTHER PUBLICATIONS

H. Kugita et al., Chemical Abstracts, 62, 6422c (1965).

George Thieme Verlag, Method of Organic Chemistry, 4th Edition, vol. V/3, pp. 715–716 (1962).

Patent Abstracts of Japan, Oct. 4, 1991, C Field; "Production of 2–chloro–4–methanesulfonyl–m–xylene", N. Tanaka, JP–A–03,161,469, Jul. 11, 1991.

Patent Abstracts of Japan, Sep. 18, 1990, C Field; "2–chloro–4–methylsufonyl–m–xylene and production thereof", T. Ishikura, JP–A–02,169,564, Jun. 29, 1990.

*Primary Examiner*—James H. Reamer
*Attorney, Agent, or Firm*—William C. Gerstenzang; Sprung Horn Kramer & Woods

[57] ABSTRACT

Alkyl-(3-chlorophenyl)-sulphones are particularly advantageously obtained by chlorination of alkylphenylsulphones if alkylphenylsulphones are chlorinated in molten form with elemental chlorine in the presence of iron(III) chloride and optionally iodine and/or sulphur.

14 Claims, No Drawings

PROCESS FOR PREPARING ALKYL-(3-CHLOROPHENYL)-SULPHONES

The present invention relates to an improved process for preparing alkyl-(3-chlorophenyl)-sulphones by chlorination of alkylphenylsulphones.

It is known that methyl-(4-methylphenyl)-sulphone can be converted into methyl-(3-chloro-4-methyl)-phenylsulphone by reaction with chlorine in the presence of antimony(III) chloride in the absence of solvent at from 85° to 90° C. (see CA 62, 6422 c (1965)). However, the product obtained by this process is contaminated by more highly chlorinated byproducts (see U.S. Pat. No. 4,675,447, page 1, line 25).

The chlorination of methyl-(4-methylphenyl)-sulphone with sulphuryl chloride in the presence of metal chlorides has been carried out at from 90° to 92° C. (see U.S. Pat. No. 4,675,447). The process results described therein have not been able to be confirmed in later work (see WO 91/07384). In addition, large amounts of catalysts are required in this process and the achievable yields lie below 80% of theory.

According to German Patent Specification 949 064, 4-alkylphenylsulphones are chlorinated in chlorosulphuric acid or sulphuric acid in the presence of copper(I) halides and iodine. This preferably produces more highly chlorinated compounds (see also Houben Weyl, Methoden der organischen Chemie, 4th edition, volume V/3, pp. 715–716 (1962)).

According to WO 91/07384, 3-chloro compounds are prepared by chlorination in sulphuric acid or oleum. Besides the dilute acid obtained, which causes problems with disposal, this process produces obviously water-soluble byproducts which pollute the waste water (see Examples 1 and 2).

There is therefore a need for an improved process for preparing alkyl-(3-chlorophenyl)-sulphones, in which the disadvantages of the known processes are avoided.

A process has now been found for preparing alkyl-(3-chlorophenyl)-sulphones by chlorination of alkylphenylsulphones, which is characterized in that alkylphenylsulphones chlorinated in molten form with elemental chlorine in the presence of iron(III) chloride. Optionally, the reaction can be carried out in the additional presence of iodine and/or sulphur.

The process of the invention is suitable, in particular, for preparing alkyl-(3-chlorophenyl)-sulphones of the formula (I)

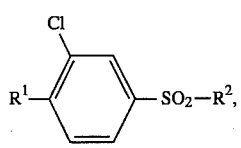

in which
R$^1$ and R$^2$ are identical or different and represent a straight-chain or branched C$_1$- to C$_4$-alkyl group, from alkylphenylsulphones of the formula (II)

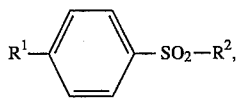

in which
R$^1$ and R$^2$ have the meanings specified for formula (I).

Particular preference is given to preparing p-methyl-(3-chlorophenyl)-methylsulphone from p-methylphenyl-methylsulphone according to the invention.

It is essential to the present invention that alkylphenylsulphones are chlorinated in molten form, i.e. without addition of acids or solvents, with elemental chlorine in the presence of iron(III) chloride and optionally iodine and/or sulphur.

The process of the invention can be carried out, for example, at from 80° to 180° C. It is preferably carried out at from 80° to 120° C., particularly preferably at from 80° to 95° C.

Preference is given to working at atmospheric pressure. It is optionally also possible to work under pressure, for example at a pressure up to 10 bar.

Chlorine is passed in, for example, at least until at least 90% by weight of the alkylphenylsulphone used have been converted, which can be established, for example, by means of gas chromatography. Chlorine is preferably passed in until between 95 and 100% by weight of the alkylphenylsulphone used have been converted. This generally requires between 4 and 16 hours.

Iron(III) chloride alone or iron(III) chloride plus iodine and/or sulphur can each be used, for example, in amounts of from 0.1 to 5% by weight, preferably from 0.2 to 2% by weight, based on alkylphenylsulphone used. This amount is preferably from 0.2 to 1% by weight. The weight ratio of iron(III) chloride to iodine and/or sulphur can be, for example, from 0.1:1 to 10:1. It is preferably from 1:1 to 5:1.

After carrying out the process of the invention, it is advantageous to blow residual chlorine out of the reaction vessel, for example with air or nitrogen.

The alkyl-(3-chlorophenyl)-sulphone prepared generally contains only small amounts of unreacted starting material and/or only small amounts of more highly chlorinated compounds. It can frequently be processed further just as it is obtained in the process of the invention. Optionally, the alkyl-(3-chlorophenyl)-sulphone prepared can be purified, for example by washing with water, distillation, fractionation and/or recrystallization.

The method of the invention generally gives alkyl-(3-chlorophenyl)-sulphones in yields of over 90% of theory.

Alkyl-(3-chlorophenyl)-sulphones are important intermediates for preparing crop protection agents (see for example EP-A 268 795).

EXAMPLES

Example 1

3.6 g of iron(III) chloride and 0.71 g of iodine were added to 190 g of molten p-methylphenyl-methylsulphone and chlorine was passed in at from 80° to 90° C. until a 95% conversion had been achieved (gas chromatographic analysis). This gave 226 g of methyl-(3-chlorophenyl)-methylsulphone having a purity of 93% by weight. This was suitable for further processing.

Example 2

The procedure of Example 1 was repeated, but continuing the chlorination until the conversion was 100%. A product having a purity of 95.5% was obtained.

Example 3

3.63 g of iron(III) chloride and 0.71 g of iodine were added to 190 g of molten p-methylphenyl-methylsulphone and 115 g of chlorine were passed in at 90° C. over a period of 11 hours. The conversion was then 95.2%. 227.5 g of methyl-(3-chlorophenyl)-methylsulphone having a purity of 92.7% were obtained (=92% of theory).

Example 4

1.6 g of iron(III) chloride and 0.31 g of iodine were added to 80 g of molten p-methylphenyl-methylsulphone and chlorine was passed in at 90° C. until the conversion was 99.8%. 102.7 g of methyl-(3-chlorophenyl)-methylsulphone having a purity of 91.8% were obtained, which corresponds to a yield of 92.2% of theory.

Example 5

(for comparison with German Patent Specification 949 064)

100 g of p-methylphenyl-methylsulphone were admixed with 20 g of 96% by weight strength sulphuric acid, and 5 mol % of copper(I) chloride and 5 mol % of iodine were added thereto and over 100 mol % of chlorine were then passed in at 30° C. Then the conversion was 27.5% and the selectivity of formation of methyl-(3-chlorophenyl)-methylsulphone was 95.9%.

Example 6

In a chlorination apparatus, 1.6 g of iron(III) chloride and 1.6 g of sulphur were added to 170 g of p-methylphenyl-methylsulphone with exclusion of atmospheric moisture and chlorine was passed in at from 80° to 90° C.

After a conversion of 99% had been achieved, the chlorine supply was turned off and residual chlorine blown out of the reaction mixture with nitrogen. After washing the crude product with dilute hydrochloric acid and water and subsequent drying, methyl-(3-chlorophenyl)-methylsulphone having a purity of over 97% was obtained in a yield of 96% of theory.

Example 7

The procedure of Example 6 was repeated, but using only 0.64 g of sulphur. This gave a 97%-pure methyl-(3-chlorophenyl)-methylsulphone in a yield of 95.5% of theory.

Example 8

The procedure of Example 6 was repeated, but using 3.24 g of iron(III) chloride and 1.24 g of sulphur. This gave a 96.5%-pure product at a conversion of 99%.

Example 9

(for comparison with WO 91/07384)

85 g of p-methylphenyl-methylsulphone were dissolved in 160 g of 96% strength sulphuric acid and chlorinated at 80° C. After a conversion of 99.5%, workup and washing to neutrality gave a 93.8%-pure methyl-(3-chlorophenyl)-methylsulphone in a yield of 89% of theory.

Example 10

The procedure of Example 6 was repeated, but without addition of sulphur. After a conversion of 98%, a 92%-pure product was obtained.

What is claimed is:

1. A process for preparing an alkyl-(3-chlorophenyl)-sulphone comprising the chlorination of an alkylphenylsulphone in molten form with elemental chlorine in the presence of iron(III) chloride.

2. The process of claim 1, in which an alkyl-(3-chlorophenyl)-sulphone of the formula (I)

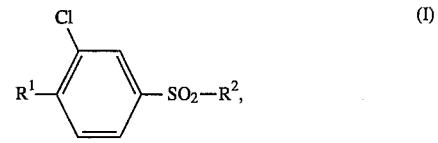

in which

R$^1$ and R$^2$ are identical or different and represent a straight-chain or branched C$_1$- to C$_4$-alkyl group, are prepared from an alkylphenylsulphone of the formula (II)

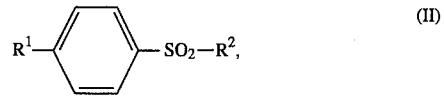

in which

R$^1$ and R$^2$ have the meanings specified for formula (I).

3. The process of claim 1, in which p-methyl-(3-chlorophenyl)-methylsulphone is prepared from p-methylphenyl-methylsulphone.

4. The process of claim 1, which is carried out at from 80° to 180° C.

5. The process of claim 1, in which chlorine is passed in until at least 90% by weight of the alkylphenylsulphone used have been converted.

6. The process of claim 1, which is carried out in the additional presence of iodine.

7. The process of claim 1, which is carried out in the additional presence of sulphur.

8. The process of claim 1, which is carried out in the additional presence of iodine and sulphur.

9. The Process of claim 1, in which iron(III) chloride is used in an amount of from 0.1 to 5% by weight, based on alkylphenylsulphone used.

10. The process of claim 1, in which iodine is used in an amount of from 0.1 to 5% by weight, based on alkylphenylsulphone used.

11. The process of claim 1, in which sulphur is used in an amount of from 0.1 to 5% by weight, based on alkylphenylsulphone used.

12. The process of claim 1, which is carried out in the presence of iron(III) chloride and at least one of iodine and sulphur and in which the weight ratio of iron(III) chloride to iodone and sulphur is from 0.1:1 to 10:1.

13. The process of claim 1, in which after carrying out the process residual chlorine is blown out of the reaction vessel.

14. The process of claim 1, in which the product obtained is purified by at least one of washing with water, distillation, fractionation and recrystallization.

* * * * *